(12) United States Patent
Gensler

(10) Patent No.: US 8,289,035 B1
(45) Date of Patent: Oct. 16, 2012

(54) METHOD AND APPARATUS FOR DETERMINATION OF ION POPULATION AND TYPE OF ION WITHIN PLANTS

(76) Inventor: William George Gensler, Tucson, AZ (US)

( * ) Notice: Subject to any disclaimer, the term of this patent is extended or adjusted under 35 U.S.C. 154(b) by 0 days.

(21) Appl. No.: 13/066,592

(22) Filed: Apr. 19, 2011

(51) Int. Cl.
*G01R 27/08* (2006.01)
(52) U.S. Cl. .......................................... 324/692; 324/72
(58) Field of Classification Search .......... 324/691–713, 324/658, 661, 686, 76.66, 519, 754.28, 750.17, 324/72, 660, 662–664; 47/49; 73/73, 304 C, 73/304 R, 304; 239/71; 205/792, 787, 777.5
See application file for complete search history.

(56) References Cited

U.S. PATENT DOCUMENTS

| | | | |
|---|---|---|---|
| 6,870,376 B1 * | 3/2005 | Gensler | 324/664 |
| 7,229,546 B1 * | 6/2007 | Gensler | 205/792 |

* cited by examiner

*Primary Examiner* — Patrick Assouad
*Assistant Examiner* — Alesa Allgood

(57) ABSTRACT

An unadjusted ion population is obtained by measurement of an unadjusted charge transfer due to an imposed electrical potential between two surfaces within a plant. An adjusted ion population is determined by dividing the unadjusted charge transfer by the wetted surface area through which the charge transfers occurs. Changes in wetted surface area are measured by changes in the electrical capacitance of the surface/liquid interface. The type of ion is identified by application of a sequence of potential values imposed on the two surfaces by a source which permits the potential of the electron emitting surface to take on a value set by the ion involved in the electron transfer. The ion is identified by the value of this potential.

4 Claims, 13 Drawing Sheets

Figure 1:

METHOD AND APPARATUS FOR DETERMINATION OF ION POPULATION AND TYPE OF ION WITHIN PLANTS

REFERENCES CITED

Gensler, W. G. U.S. Pat. No. 6,870,376 (2005)
Gensler, W. G. U.S. Pat. No. 7,229,546 (2007)
Gensler W. G. U.S. Pat. No. 3,967,198 (1976)
Bard, A. J. and L. R. Faulkner (1980) Electrochemical Methods, Fundamentals and Applications, Wiley, New York.
Bard, A. J. and L. R. Faulkner (2001) $2^{nd}$ Edition. Electrochemical Methods, Fundamentals and Applications, Wiley, New York.
Bockris, J O'M and A. K. N. Reddy (1973) Modern Electrochemistry. Plenum Press, New York.
Cavicchi, T. J. (1992) Fundamentals of Electrical Engineering. Prentice Hall, Englewood Cliffs, N.J.
Davis, V., A. Shigo and R. Weyrick (1979). Seasonal changes in electrical reisistance of inner bark in Red Oak, Red Maple and Eastern White Pine. Forest Science, Vol. 25, #2, pp. 282-286.
Evert, R. Esau's Plant Anatomy, $3^{rd}$ Edition. (2006). Wiley and Sons, Inc. Hoboken, N.J.
Gagnon, R. R., E. Bauce and M. Pineau (1987) Relation between water potential and cambial electrical resistance of balsam fir and white spruce after budbreak. Canadian Journal of Forest Research 17:105-108.
Gensler, W. G. (1999) Measuring and interpreting diurnal activity in the main stem of trees. In Tree Ring Analysis, Biological, Methodological and Environmental Aspects, SectionA, Chapter 3. R. Wimmer and R. E. Vetter, Eds. CABI Publishing, Oxford, UK
Hoare, J. (1968). The electrochemistry of oxygen. Wiley, N.Y.
Ike, G. W. Thurtell and K. R. Stevenson (1978) Evaluation of the pressure chamber technique for measurement of leaf water potential in cassaya (*Manihot* species). Canadian Journal of Botany, 56:1638-1641.
Lekas, T. M., G. MacDougal, D. A. Maclean and R. G. Thompson (1990) Seasonal trends and effects of temperature and rainfall on stem electrical capacitance of spruce and fir trees. Canadian Journal of Forest Research 20:970-977.
MacDougall, R. G., R. G. Thompson and H. Piene (1987) Stem Electrical capacitance and resistance measurements as related to total foliar biomass of balsam fir trees. Canadian Journal of Forest Research 17:1071-1074.
MacDougall, R. G., D. A. Maclean and R. G. Thompson (1988) The use of electrical capacitance to determine growth and vigor of spruce and fir trees and stands in New Brunswick. Canadian Journal of Forest Research 18:587-594.
Piene, H., R. G. Thompson, J. E. McIsaac and D. S. Fenson (1984). Electrical resistance measurements on young balsam fir trees in relation to specific volume increment, foliar biomass, and ion content of bark and wood. Canadian Journal of Forest Research 14:177-180.
Silva-Diaz, F., W. Gensler and P. Sechaud (1983) In vivo cyclic voltammetry in cotton under field conditions. Journal of the Electrochemical Society, Vol 130, #7, pp 1464-1468.
Smith, K. T. and W. D. Ostrofsky (1993). Cambial and internal electrical resistance of red spruce trees in eight diverse stands in northeastern United States. Canadian Journal of Forest Research 23: 322-326.
Taiz, L. and E. Zeigler (2006). Plant Physiology, $4^{th}$ Ed. Sinauer Associates, Sunderland, M A
Tattar, T. A Shigo and T. Chase (1972). Relationship between the degree of resistance to a pulsed electric current and wood in progressive stages of discoloration and decay in living tissue. Canadian. Journal of Forest Research 2:236-243.
Traynor, J. ((2003) Leaf vs. Petiole Analysis to find "N" in Grapes. Grape Grower Magazine,

FIELD OF THE INVENTION

This invention concerns measurement of ion population and identification of the type of ion within a plant

SPECIFICATION

Prior Art Concerning Measurement of Resistance and Conductivity in Plants

Non destructive measurements of resistance and conductivity in plants have been performed extensively (Davis, V., A. Shigo and R. Weyrick (1979); Tattar, T. A Shigo and T. Chase (1972); Piene, H., R. G. Thompson, J. E. McIsaac and D. S. Fenson (1984); Smith, K. T. and W. D. Ostrofsky (1993); Gagnon, R. R., E. Bauce and M. Pineau (1987); R. G. MacDougall, R. G. Thompson and H. Piene (1987); MacDougall, R. G., D. A. Maclean and R. G. Thompson (1988); Lekas, T. M., G. MacDougal, D. A. Maclean and R. G. Thompson (1990)). In these measurements there was no attempt to delineate the causative reactant leading to the overall value of resistance or conductivity. In addition, the measurements were not made concomitant with separate measurements of electrical capacitance. The apparatus was based on the model of the medium between the two surfaces as a resistor and capacitor in parallel. The methods and apparatus then determined the value of the resistor and capacitor. Efforts were also not directed to a determination of any specific origin of the resistance or capacitance, only the variation of the resistance and capacitance with gross plant characteristics such as growth rate.

There was also no attempt to distinguish between the conductivity of the extracellular fluid and the conductivity of the tissue volume as a whole.

Difference in the Prior Art of U.S. Pat. No. 6,870,376, U.S. Pat. No. 7,229,546 and this Invention
Concerning Direction of Energy Flow Prior art consists of placement of surfaces within the plant and in the root zone. Electrochemical devices are then connected to these surfaces. The apparatus consists of the surfaces and an external electronic device. The methods applied to this apparatus fall into two categories: the apparatus is operated as a galvanic cell or an electrolytic cell. There is fundamental difference between these two types of cells. In a galvanic cell, energy flows from the region around the surfaces to the external electronic device. In an electrolytic cell energy flows from the external electronic device to the surfaces and the region between the surfaces. This distinction is clearly illustrated in medicine. An electrocardiogram employs surfaces placed on the patient and an electronic device connected to these surfaces. Energy flows from the region between these surface through the surfaces and into the electronic device. This is an example of a galvanic cell. In a heart pacemaker, there are surfaces implanted around the heart and an electronic device implanted within (at the present time) the patient. Energy flow is from the implanted electronic device into the surfaces. The electrocardiogram and heart pacemaker both utilize surfaces on or in the patient and an electronic device. The difference in the direction of the flow of energy cannot be taken lightly. An electrocardiogram is basically observational, that is, it supplies information concerning the patient. By contrast, one does not "observe" a heart pacemaker. The heart pacemaker performs active electrochemistry within the patient. The methods and apparatus of the two devices are completely different. To this day there is no device employing a hybrid technology in medicine, that is, an interactive electrolytic and galvanic cell to achieve a single objective.

Prior art as seen in these two patents and this invention are examples of these same two categories of electrochemical cells with regard to plants. The method in the two patents is observational. The methods are examples of galvanic cells. By contrast, the method in this invention is hybrid, that is, interrelated electrolytic and galvanic cells are employed. The apparatus performs active electrochemistry within the plant. It involves an electrolytic cell to set up the conditions within the plant for observations using a galvanic cell. Transfer of electrical energy into the plant must be accomplished at levels low enough and at widely spaced intervals to insure insignificant disruption of normal metabolism. The methods in this invention must be applied hourly over periods of months and years. Both the electrolytic cell and the galvanic cell must be non disruptive.

The determination of water content and sucrose transport in U.S. Pat. No. 6,870,376 and U.S. Pat. No. 7,229,546 are examples of galvanic cells. There is no prior art in plants wherein the apparatus and method is a hybrid combination of galvanic and electrolytic cells. By contrast, this invention is such a combination of galvanic and electrolytic cells applied to the determination of adjusted ion population and identification of the type of ion.

Figure 4A:
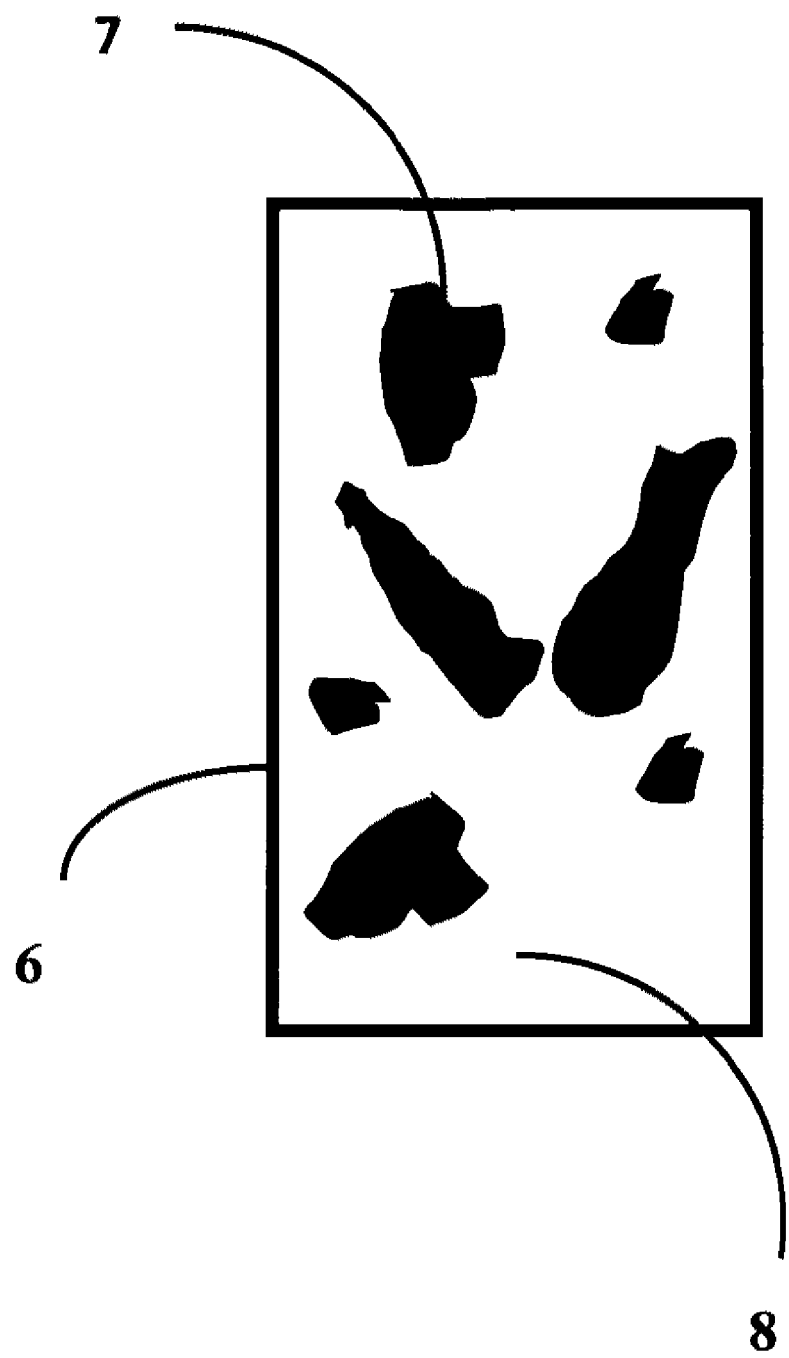

Concerning the Components of the Area of the Surface within the Plant and their use in the Prior Art of U.S. Pat. No. 6,870,376, U.S. Pat. No. 7,229,546 and in This Invention FIG. 4a illustrates the different characteristics of a surface implanted in a plant. The surface within a plant has a total surface area 6, a wetted area 7 and a dry area 8. The addition of the wetted surface area 7 and dry surface area 8 yields the total surface area 6. The capacitance value in U.S. Pat. No. 6,870,376 is proportional to the wetted surface area 6. This value is then adjusted by forming a ratio of the capacitance value to the total surface area 6. Adjustment is necessary to take into account the variable residence area of the implants of the surface within the plant. For example, implant of a surface through the stem of a branch is going to yield greater capacitance values than implant in the stem of a leaf. This is simply because the length of sensor within the branch is greater than in a leaf. This will be the case even when the water content of the tissue surrounding the surface is the same in the branch as in the leaf. This difference is taken into account by forming the ratio of the measured capacitance by the total area of the surface 6 within the plant.

In this invention, the greater the wetted surface area, the greater the charge transfer at the same impressed potential and the same ion population. This requires that the charge transfer be adjusted to take into account the difference in wetted surface area 7 over the diurnal cycle, the seasonal cycle and any anthropogenic influences such as irrigation.

This adjustment is made by dividing the unadjusted measured net charge transfer by the wetted surface area 7. The value of wetted surface area 7 is obtained by a measurement of electrical capacitance. This permits an adjusted net charge transfer to be reached by forming a ratio of the unadjusted net charge transfer and the measured capacitance.

In summary, the area in U.S. Pat. No. 6,870,376 is the total surface area 6 measured with a digital caliper and wetted area 7 measured in terms of electrical capacitance. The output variable is the ratio of these two quantities in units of farads/millimeter. In this invention the output variable is a ratio of unadjusted net charge transfer divided by wetted area 7 in units of coulombs/farad. The dimensions of these two variables are a clear indication that U.S. Pat. No. 6,870,376 and this invention are basically different.

Prior Art Concerning Identification of the Type of Ion in the Plant

A widely practiced method of determining the level and identification of the type of ion in plants is the so-called "petiole analysis." (Traynor, 2003) In this method a sample is formed from cuttings of petioles or other parts of the plant. The sample is sent to an off-site laboratory. At the laboratory, the sample is ground up and an assay is made of the amount of the various constituents in the sample, for example, the presence and level of nitrogen, potassium, calcium etc.

A method of identification of the constituents of the extracellular fluid which is not destructive and which only considers the extracellular fluid was published in a paper by Silva-Diaz, Gensler and Sechaud (Silva-Diaz, et al, 1983). This method employed a surface in the plant and a surface outside the plant apposed to the plant surface. The surface outside the plant was fixed relative to the standard hydrogen electrode. The potential of the surface inside the plant was forced to sweep over a potential range between about one thousand millivolts positive and negative relative to a standard silver chloride reference electrode. Current levels were recorded continuously over the sweep. Surges in current were indicative of the presence of a constituent in the extracellular fluid with an electron energy level corresponding to the potential of the surface inside the plant relative to the silver chloride reference electrode.

The method and apparatus in this invention is fundamentally different from the Silva-Diaz apparatus and method. In this invention, there are two contiguous surfaces located within the plant, not one surface as in the Silva-Diaz apparatus. In this invention there is a third surface in the root zone. In the Silva Diaz apparatus there is no surface located in the root zone.

The electrochemical circuit path in the Silva-Diaz method begins at a wire from the electronics. This wire is connected to a surface inside the plant. The path then moves through the plant for a distance in the order of about twenty centimeters, crosses outside the plant surface to a salt bridge apposed to the surface (essentially a salted liquid path held in a cotton matrix). The other end of the salt bridge is immersed in a solution in a beaker. Then the path continues through the solution in the beaker to a second surface. The second surface is connected to the electronics (see FIG. 1 in the cited paper).

In the Silva-Diaz method, a variable potential is imposed between the surface within the plant and second surface located in the solution in the beaker outside the plant. This potential of the latter surface is fixed or tethered to a standard reference electrode (see FIG. 1 of the cited paper). The imposed potential sweeps over a range of positive and negative values. There is an entire sequence of different reactions at the different values of imposed potential. The Silva-Daiz method is an example of the method termed linear sweep voltammetry (Bard and Faulkner, 2001, Chapter 6). The term "sweep" in this case is used to describe the sequence of different value of imposed potential. This leads to the conventional ion identification technique based on matching the observed current pulses to a known value of imposed potential. For example, current surges were observed at values of potential known to be potentials wherein oxides of the noble metal surface material itself form. There is a single electrochemical path. The surfaces and electronics in the Silva-Diaz apparatus form an electrolytic cell.

Identification of the type of ion in this invention is different from the Silva-Diaz method. There are two surfaces located within the plant and a third surface in the root zone (see FIG. 2).

Figure 3A:
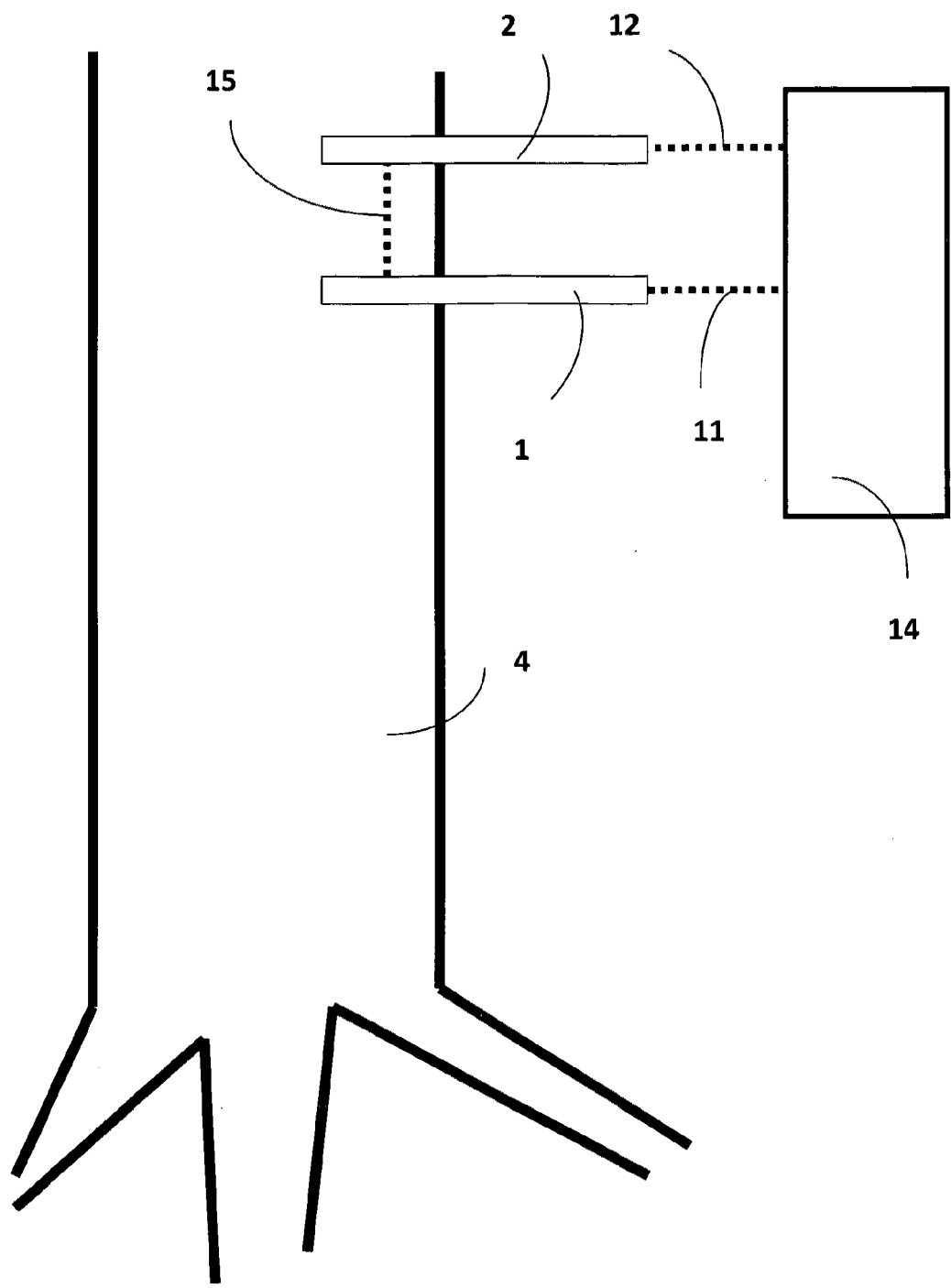
Figure 3B:
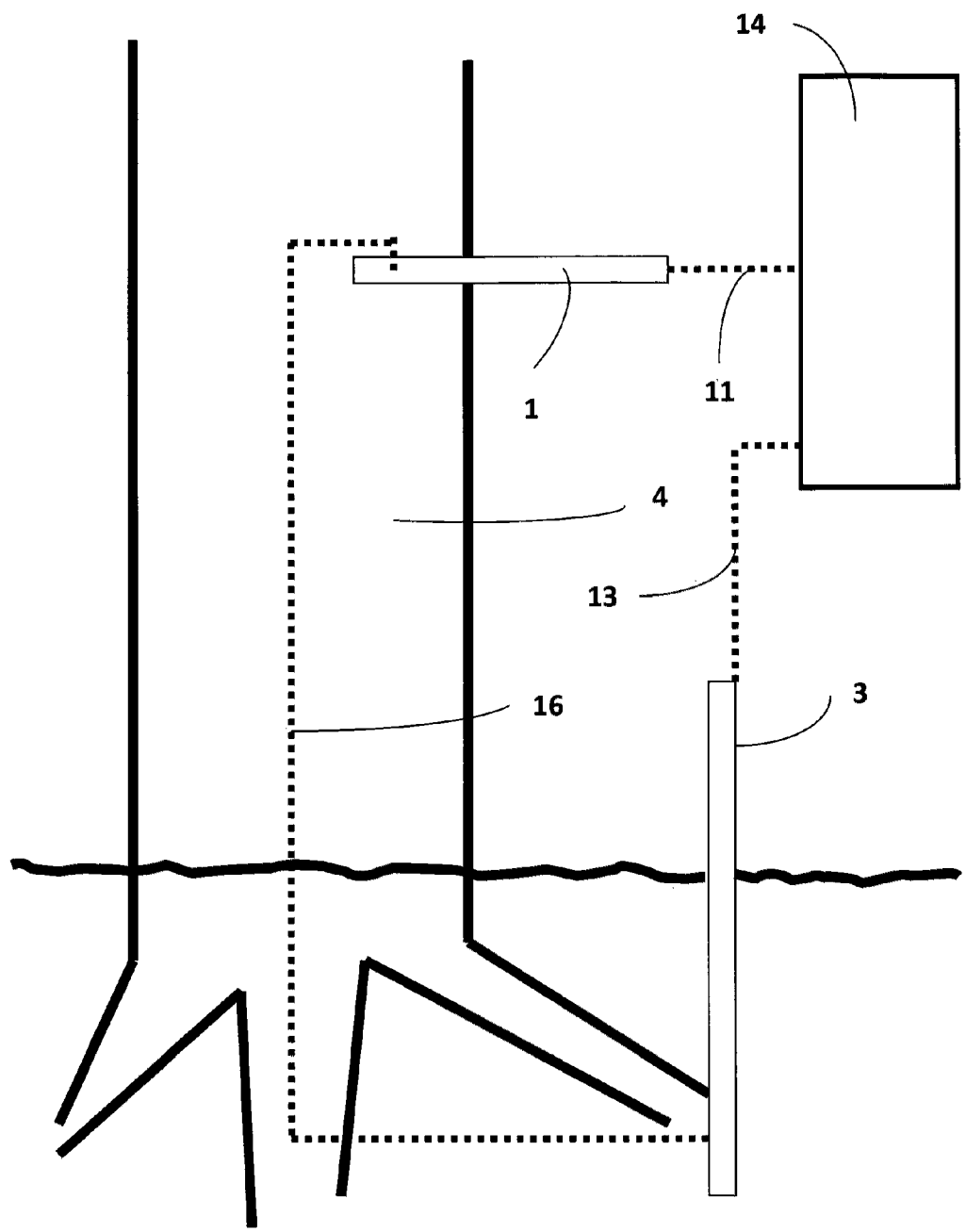
Figure 3C:
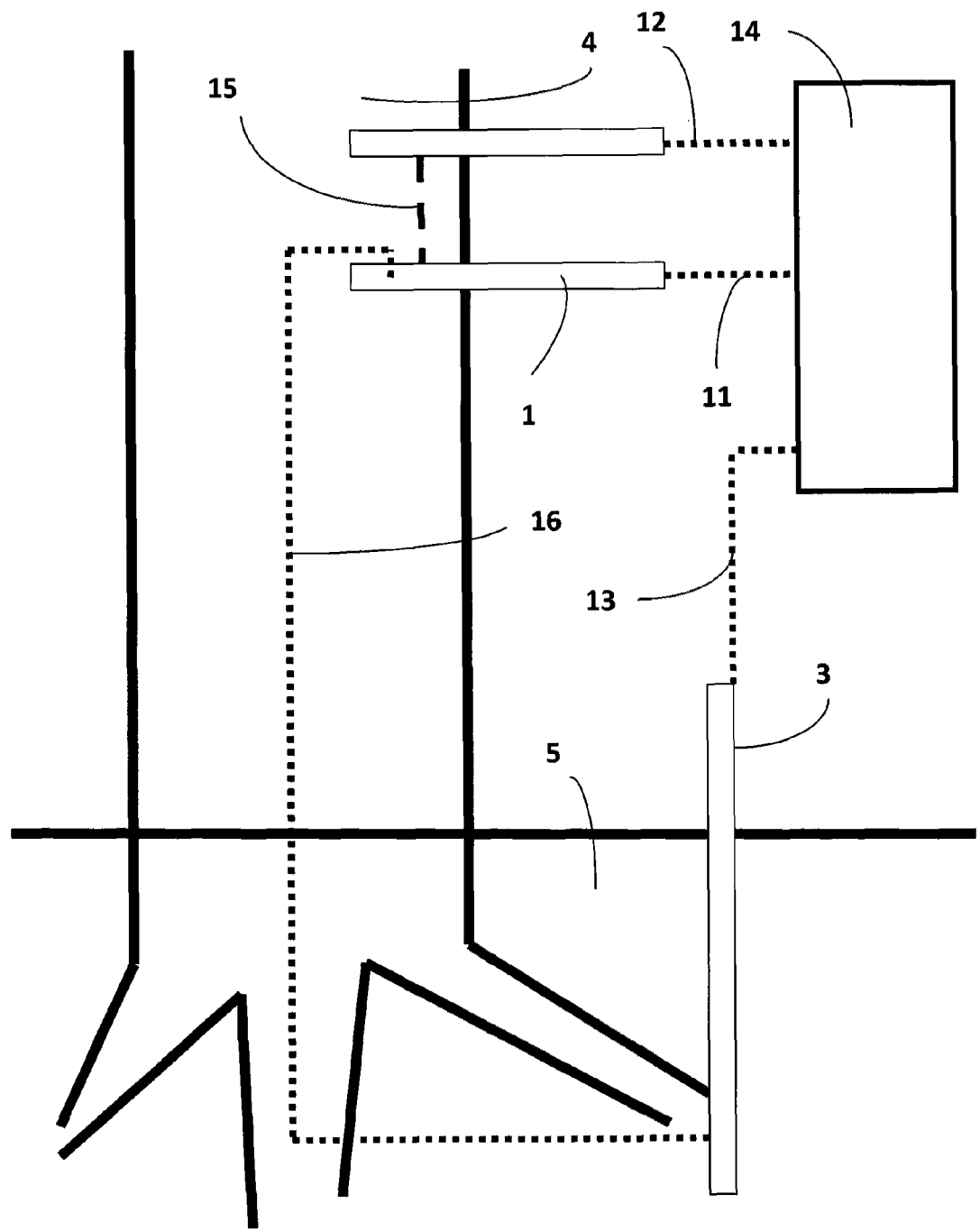

There are two electrochemical paths in this invention (See FIGS. 3a and 3c). The first path is between first surface 1 and second surface 2 in the plant and the electronics 14. This assembly forms an electrolytic cell (see Definition of Terms). The second path is between first surface 1 in the plant and third surface 3 in the root zone and the electronics 14. This assembly forms a galvanic cell (See Definition of Terms). Identification is accomplished by a determination of an extrapolated value of potential of a galvanic cell, not a match between current and potential of an electrolytic cell as in the Silva-Diaz method.

In the Silva-Diaz method, the electronics is fixed with respect to a reference electrode outside the plant and/or root zone. In this invention the surfaces within the plant and the potential source are allowed to float, that is, they are untethered relative to any ground electrode or reference electrode connected to the ground electrode. The energy of the ions in the liquid between the two surfaces sets the potential of the metal/liquid interface. Changes in this galvanic potential can be measured during a sequence of values of imposed potential of the electrolytic cell. The measurement of these changes is accomplished by a measurement of the potential of first surface 1 within the plant relative to third surface 3 in the root zone. There is no sweeping of the potential of this galvanic cell. In other words, the cause of any change in potential of the galvanic cell is the sequence of different values of imposed potential of the electrolytic cell.

From an energy viewpoint, the energy of the ions within the fluid sets the potential of the galvanic cell. This is in distinction to an outside source imposing a potential on the liquid in an electrolytic cell as in the Silva-Diaz method.

In this invention, identification of the type of ion takes the form of matching the observed energy level of the ions in the liquid to the type of ion addition to the root zone and upward into the plant. In the Silva-Daiz method identification of the ion is set by the value of potential concomitant with the current surges during the potential sweep.

The method in this invention also differs from the Silva-Daiz method in the determination of the equilibrium potential associated with a particular reactant. The equilibrium potential is arrived at by extrapolation from a plot of the sequence of overpotential measurements against the sequence of cell potential values. The value obtained by this extrapolation is a value at zero overpotential. The value also is not influenced by the value of pH. The value of potential in the Silva-Diaz method is an algebraic combination of the equilibrium potential and a non zero overpotential. Furthermore, the value in the Silva-Diaz method is influenced by the proton concentration of the liquid.

Concerning the Utility of the Apparatus and Method in the Prior Art of U.S. Pat. No. 6,870,376, U.S. Pat. No. 7,229,546 and This Invention The utility of U.S. Pat. No. 6,870,376 is a measure of water content inside the plant. A knowledge of water content and changes in water content provide quantitative guidance for irrigation scheduling. This Patent is about water.

The utility of U.S. Pat. No. 7,229,546 is a measure of sucrose transport between different regions of the plant. A knowledge of the rate of sucrose transport results in a knowledge of rate of growth and particularly rate of fruit development. Cultural practice is then adjusted to optimize this rate.

The utility of this invention is a quantitative indication of the ion population and identification of the type of ion within a plant 24/7 for the full calendar year. This will result in a chronology of storage and uptake. This will permit addition of specific fertilizer to the root zone that matches the chronology of storage and usage of the fertilizer in the plant. It further minimizes the loss of fertilizer due to leaching to the water table. Fertilizer will be applied only when the plant takes up the fertilizer. This invention is about fertilizer

OBJECTS AND ADVANTAGES

Novel Characteristics of this Invention to Determine Ion Population in the Plant Prior art measures ion population by measuring conductivity and resistance in the plant. Prior art does not quantitatively adjust the measured conductivity and resistance values for the area of the metal/solution interface through which charge transfer occurs. Charge transfer can only occur across wetted surfaces. The wetted surface area is only assumed. This invention makes a direct measurement of the wetted surface area through which charge transfer occurs and adjusts the charge transfer values to take into account variability in this area during diurnal and season cycles as well as anthropogenic influences such as irrigation.

The further novelty is the use of the capacitance of the parallel plate capacitor at the net charge transfer metal/liquid interface to achieve a value that is proportional to this wetted surface area.

Novel Characteristics of this Invention Compared to Prior Art Identification of the Type of Ion in a Plant.

Prior art in the identification of the type of ion employs apparatus consisting of one surface in the plant and one surface outside the plant and electronics in a single electrolytic cell. The surface outside the plant is fixed or tethered to a known reference potential. A variable potential is impressed across the two surfaces. Current pulses occur at different values of this potential due to a reactant transferring charge across the metal/liquid interface in the plant. The potential at which these current pulses occur identifies the type of ion present in the region between the surfaces.

By contrast, this invention utilizes three surfaces: two in the plant and one in the soil These surfaces are used in two electrochemical cells: an electrolytic cell and a galvanic cell. In the electrolytic cell electronics impresses a sequence of potential values between the two surfaces within the plant. The two surfaces and electronics are not fixed or tethered to a known reference potential. The circuit is allowed to "float." The second electrochemical circuit is a galvanic cell that measures a second sequence of potentials of one of the surfaces in the plant with respect to the surface in the soil. The value of potential that would ensue at zero value of impressed potential between the two surfaces in the plant identifies the type of ion in the region between the two surfaces in the plant.

Definition of Terms:

1. Inside-the-plant 4 is defined as a homogeneous volume of plant tissue filled with normal functioning cells between first surface 1 and second surface 2.

2. Soil 5 is defined as a volume containing the root mass of the plant

3. Ion population is defined conceptually as the presence of individual reactants such as nitrate, potassium, or phosphorus in the extracellular liquid of a plant. Ion population is defined operationally in terms of a measurement as the number of electrons that cross first surface 1 in response to an applied potential between first surface 1 and second surface 2.

4. Charge transfer is defined as the number of charges crossing the liquid/metal interface in a single direction.

5. Type of ion is defined as the specific ion which is the dominant constituent of the ion population; for example, nitrate or potassium.

6. Overpotential is defined as the increase or decrease in the magnitude of the potential between the metal and bulk solution present at a surface/fluid interface when there is non zero net charge transfer across the interface. (Bockris and Reddy, Volume 2, page 883); Bard and Faulkner, 1980, Eqn. 1.3.5). In this invention it is the change in potential between wire 11 with respect to wire 13 under non zero net charge transfer conditions under the assumption that the potential change across the third surface 3/solution interface is constant.

7. Equilibrium potential is defined as the value of potential across the metal and bulk solution interface associated with a particular reaction at the zero net charge transfer condition of that reaction. Operationally, it is the value of potential of the intercept of the second sequence of measured potential across first surface 1 and third surface 3 at zero net charge transfer. (See also, Bard and Faulkner, 1980, Eqn 1.3.5)

8. First sequence of potential values are values of potential of second surface 2 with respect to first surface 1. This is the "impressed potential" described in the claims 9. Second sequence of potential values are values of potential of first surface 1 with respect to third surface 3.

10. Extrapolated value is the value of the potential of first surface 1 with respect to third surface 3 as the value of the first sequence of potential values is reduced to zero.

11. Galvanic Cell is defined as an assembly consisting of two surfaces immersed in a solution and electronics connected to the surfaces wherein energy transfer is from the solution between the surfaces to the electronics. (See Bard and Falkner, $2^{nd}$ Ed. 2001, page 18)

12 Electrolytic Cell is defined as a assembly consisting of two surfaces immersed in a solution and electronics connected to the surfaces wherein energy transfer is from the electronics to the solution between the surfaces. (See Bard and Falkner, $2^{nd}$ Ed. 2001, page 18)

13. Fertigation is the process of applying irrigation water impregnated with fertilizer.

Measurements, Determinations and Identifications of This Invention

The apparatus in this invention are used to make the following three measurements 1. Electrical capacitance between first surface 1 and second third surface 3 under zero net charge transfer
2. Unadjusted net ion charge transfer between first surface 1 and second surface 2
3. Potential of first surface 1 with respect to third surface 3 under non zero net charge transfer This invention makes the following determination using the above measurements:

1. Determination of an adjusted net charge transfer from the ratio of the measurements of unadjusted net charge transfer and electrical capacitance.

This invention makes the following identification:

1. Identification of the type of ion within an ion population from the extrapolated value of a second sequence of values of potential of first surface 1 with respect to third surface 3 as the first sequence of potential values between first surface 1 and second surface 2 goes to zero.

Specific Aspects of the Apparatus and Methods (a) Location of First Surface 1, Second Surface 2 and Third Surface 3

Figure 2:
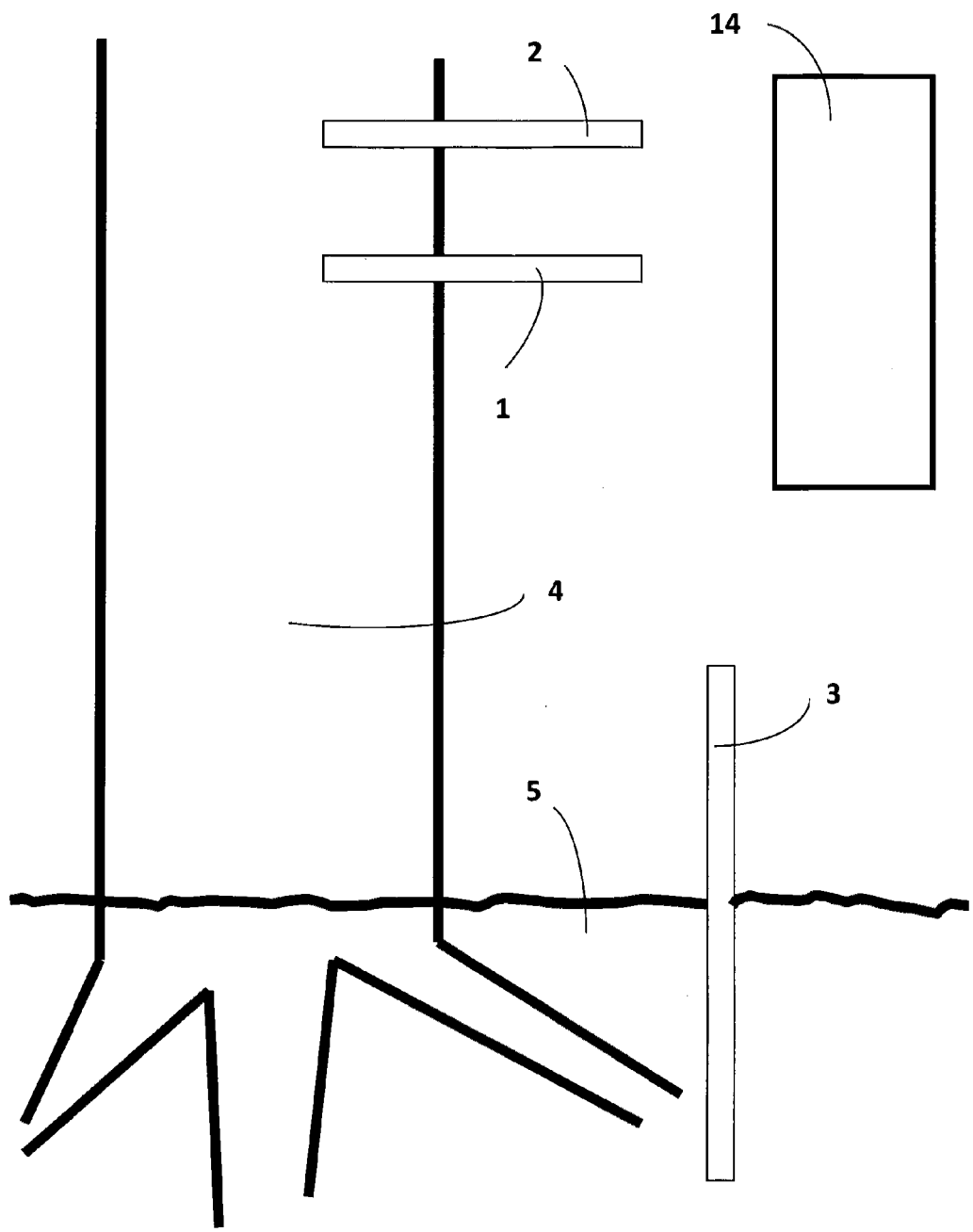

FIG. 2 illustrates the three surfaces of the apparatus in locations in plant 4 and soil 5. First surface 1 and second surface 2 are implanted in the any part of plant 4. A common location is the sapwood of the trunk. Third surface 3 resides in soil 5.

The distance between first surface 1 and second surface 2 should be such that the tissue between the surfaces is functionally homogeneous. A typical distance is about two to three millimeters.

The physical size of first surface 1 and second surface 2 should be such that the insult to the tissue does not result in a tissue reaction that would interfere with normal metabolism in the cells surrounding the surfaces. For example, scar tissue should be avoided. This leads to a shape of first surface 1 and second surface 2 that is round with diameters in the order of tens of micrometers. Third surface 3 is normally a twelve mm diameter, 244 cm long copper clad stainless steel grounding rod buried to within 10 cm of the soil surface. This placement results in minimal reaction changes at the surface of the rod.

(b) Electrochemical Circuit Paths

The circuit path for the impressed potential is shown in FIG. 3$a$ in dashed lines. The path begins in the electronics 14, proceeds through wire 11, enters first surface 1, moves through first surface 1, crosses the first surface 1/liquid interface, moves through plant 4 along a path 15, crosses second surface 2/liquid interface, moves through second surface 2, proceeds through wire 12 and returns to electronics 14. Energy flow for this path is from electronics 14 to plant 4. This circuit causes net charge transfer across the two interfaces. Electrons are emitted from first surface 1 and collected at second surface 2. The electronics has two functions. The first function is to generate a sequence of potential levels between wire 12 and wire 11. The second function is to measure the net charge transfer through wire 11 that accrues from this impressed potential.

The circuit path for the capacitance measurement is shown in dashed lines in FIG. 3$b$. The path begins in the electronics 14, proceeds through the wire 13, enters third surface 3, moves through third surface 3, crosses the third surface 3/liquid interface, moves through plant 4, crosses first surface 1/liquid interface, moves through first surface 1, proceeds through wire 11 and returns to electronics 14. Energy flow for this path is from plant 4 to electronics 14. The function of this path is to measure the capacitance between wire 11 and wire 13. This measurement is made at zero net current transfer in the circuit path for impressed potential described immediately above. This fact is emphasized in FIG. 3$b$ by the omission of second surface 2.

The circuit path for the potential measurement is shown in FIG. 3$c$. It is the same as the circuit path for the capacitance measurement. By contrast to the capacitance measurement, this potential measurement is made only when there is net charge transfer in the circuit path for impressed potential described above. In other words, this potential measurement is made only when there is net charge transfer across the first surface 1/liquid interface. The reason for this is that an overpotential exists at the first surface 1/liquid interface only when there is net charge transfer across the interface. The path has been drawn with a short vertical path moving out of the surface upwards towards second surface 2. This figuratively indicates the "location" of the overpotential.

The potential measurement is made only when there is a non zero net charge transfer. This fact is emphasized in FIG. 3c by the inclusion of the charge transfer path 15 between first surface 1 and second surface 2 in the figure.

(c) Charge Movement across First Surface 1/Water Interface and Second Surface 2/Water Interface FIG. 4a illustrates the presence of wetted area 7 and dry area 8 within the total surface area 6 of first surface 1 or second surface 2.

Figure 4B:
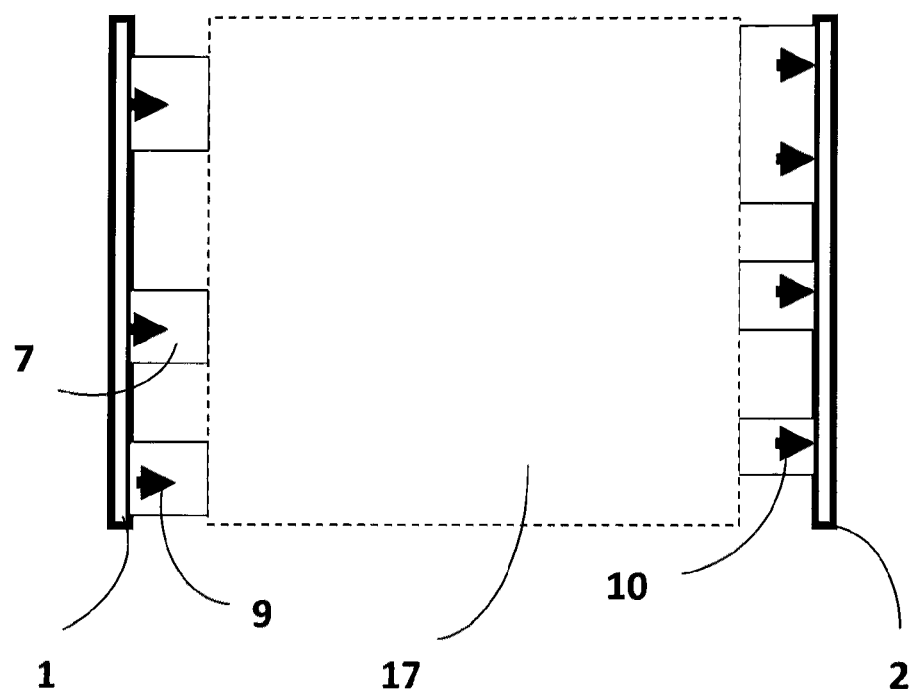

FIG. 4b illustrates schematically (as if they were both flat surfaces) first surface 1 facing second surface 2 with adsorbed water on both surfaces. The arrows at first surface 1 illustrate electrons moving from first surface 1 to reactants in the adsorbed water. At second surface 2, the arrows illustrate electrons moving from the reactants in the adsorbed water to second surface 2. The movement of electrons takes place only in parts of first surface 1 and second surface 2 that are covered with adsorbed water.

The significant aspect of FIG. 4b is the movement of charge only in the wetted area of the cells. This area is quantified by the measurement of electrical capacitance.

FIG. 4b illustrates the essential characteristic of first surface 1 and second surface 2. These surfaces function as windows inside-the-plant through which one can observe the activities of the mass of cells between the surfaces. Both chemical and physical characteristics of the mass of cells can be observed by passive measurements of water content and active measurements employing electrical potential. The electric field set up by impressing a potential between the surfaces elicits movement of the charge within this mass and permits a determination of the presence of charge within the mass.

(d) Use of Electrical Capacitance as a Measure of Wetted Surface Area

The electrical capacitance measurement is used as an indicator of the wetted area of first surface 1. This use of this area taught in U.S. Pat. No. 6,870,376 is quite different. Assuming an equilibrium between this wetted surface area and the water content of the plant tissue surrounding the surface, the wetted surface area becomes a measure of plant water content. The use of wetted surface area in this invention is more intrinsic. It gives a measure of charge transfer area of the surfaces within the plant. FIG. 4a is a schematic illustration of first surface 1 as if it were a flat surface 6. This figure illustrates the strong differences in the presence of water in discrete regions of first surface 1 inside-the-plant. Region 7 is the wetted area; region 8 is dry area. At any one time, the summation of these individual areas is the total wetted surface area 6. The water on the surface is adsorbed. The total wetted surface area 6 changes throughout the twenty-four hour cycle.

Only the wetted surface contributes to the interfacial capacitance at the surface/water interface. The wetted area is a maximum when the entire area of first surface 1 is wetted.

The electrochemical origin of the capacitance between first surface 1 and the fluid around it is a layer of ionized oxygen in the adsorbed water on first surface 1 (Hoare, 1968). This layer forms one layer of a parallel plate capacitor. The opposing layer is a layer of electrons within first surface 1. The total capacitance arises from capacitors at first surface 1 and third surface 3. The capacitance arises only secondarily from a polarization of the dielectric material between the two surfaces. An assumption is made that the capacitance of third surface 3/soil interface is constant. Any changes in capacitance are attributed to changes at the first surface 1/liquid interface. This assumption is based on the physical location of third surface 3 deep within the soil such that changes at the third surface 3/soil interface are minimal.

Since a capacitance of the parallel plate capacitor is proportional to the area of charged plates, the interfacial capacitance is proportional to changes in the wetted surface area. Mathematically, the capacitance measurement is based on the presence of two apposing layers of electric charge, a layer of ionized oxygen in the adsorbed water and a layer of electrons on first surface 1. The capacitance of this physical array of charges is given by (Eqn 2.28, Cavicchi, T, 1992)

$$Capacitance = area\ of\ the\ charged\ plate * permittivity / distance\ between\ plates$$

The permittivity of the adsorbed water is constant and the distance between the plates is constant. This means the capacitance is directly proportional to the area of the charged plate. But the area of the charged plate is the wetted area of first surface 1.

$$Capacitance = wetted\ surface\ area * permittivity / distance\ between\ plates$$

$$Capacitance = wetted\ surface\ area * K$$

This means that an adjusted net charge transfer can be formed by dividing the unadjusted net charge transfer by the measured capacitance as follows:

$$adjusted\ net\ charge\ transfer = unadjusted\ net\ charge\ transfer / wetted\ surface\ area$$

$$adjusted\ net\ charge\ transfer = unadjusted\ net\ charge\ transfer / (measured\ capacitance / K)$$

where K is a constant of proportionality

This calculation makes the assumption that the capacitance of third surface 3/liquid interface is constant. Any change in measured capacitance arises from a change in the first surface 1/liquid interface Identification of Type of Ion The identification method has to work within a definite set of constraints. First surface 1 and second surface 2 are inside the plant and not visible. The only thing known about the surfaces are the size of total surface area 6 illustrated in FIG. 4a, the composition of the surface material and the tissue type surrounding the surfaces. The electron transfer reactions at both first surface 1 and second surface 2 are not known. The fluid transfer path between the surfaces is only through the extracellular region. This is about 5% of the total volume of the tissue (Evert, 2006, Taiz and Ziegler, 2006).

The identification procedure is based on the fact that each type of ion has a definite electron energy level. For example, the nitrate ion, $NO_3$, is negatively charged. This negative charge has a definite energy level compared to the energy level of a potassium ion. This method uses the difference in these energy levels to identify the presence of the ion in the extracellular fluid.

The matching of the ion to the observed energy level of the electrons in the fluid must be indirect since all of the measurements are made in-vivo and non destructively.

Under field conditions, the extrapolated value is obtained over an extended period (termed the quiescent mode) wherein there is no anthropogenic influence on the field such as irrigation. The field is simply not subjected to man-made influences. Then when a man-made influence is imposed on the field, e.g., irrigation, a surge of uptake of water occurs. This water will bring up nutrients in many cases. The extrapolated value is again obtained. Identification is made by comparison of the extrapolated value obtained before a period of water uptake with the extrapolated value during the period of water uptake.

Example of the Chronology of Measurements, Determination and Identification, Five Day Time Scale FIG. 5a-5d illustrate the chronology (measurements every hour) in an almond orchard in Kern county, California over a five day period from 5 Jun. to 10 Jun., 2012:

5 June: Orchard is a quiescent mode. Soil water content near constant; sapwood water content exhibiting normal diurnal cycles of water content 6 June, 0000 hours: measurement of capacitance of first surface 1, measurement of second sequence of potential (diamonds in FIG. 5c), determination of extrapolated potential (intercept potential shown in dashed line in FIG. 5c); quiescent mode continues.

7 June, 0700 hours: Irrigation begins. Plant water content rises.

8 June, 0000 hours: measurement of capacitance of first surface 1, measurement of second sequence of potential (squares in FIG. 5c), determination of extrapolated potential (intercept potential shown in dashed line in FIG. 5c); irrigation mode continues.

9 June, 0800 hours: Irrigation stops. Plant water content falls. Quiekent mode resumes.

The extrapolated potential is the value of potential at the intersection of the regression line of the second sequence of potential values with the intercept potential. The extrapolated value is used to identify the type of nutrient. There was a 200 my difference between the extrapolated value in the quiescent mode and the extrapolated value during the irrigation. The regression lines for two individual hourly measurement before and during irrigation are given in FIG. 5c.

The potential between first surface 1 and second surface 2 had seven steps: 100, 166, 231, 296, 362, 428, and 496 mV. This value was impressed for 200 mseconds. This is an example of the first sequence of potential values stated in the claims. A measurement of the second sequence of potential values is made at the end of each of these seven steps.

The net charge transfer that occurred during the 200 msecond period was also measured at the end of each of these seven steps. Before each step, there is a short equilibration period to permit double layer equilibration (Bard and Faulkner, 2001, page 14).

Figure 5A:
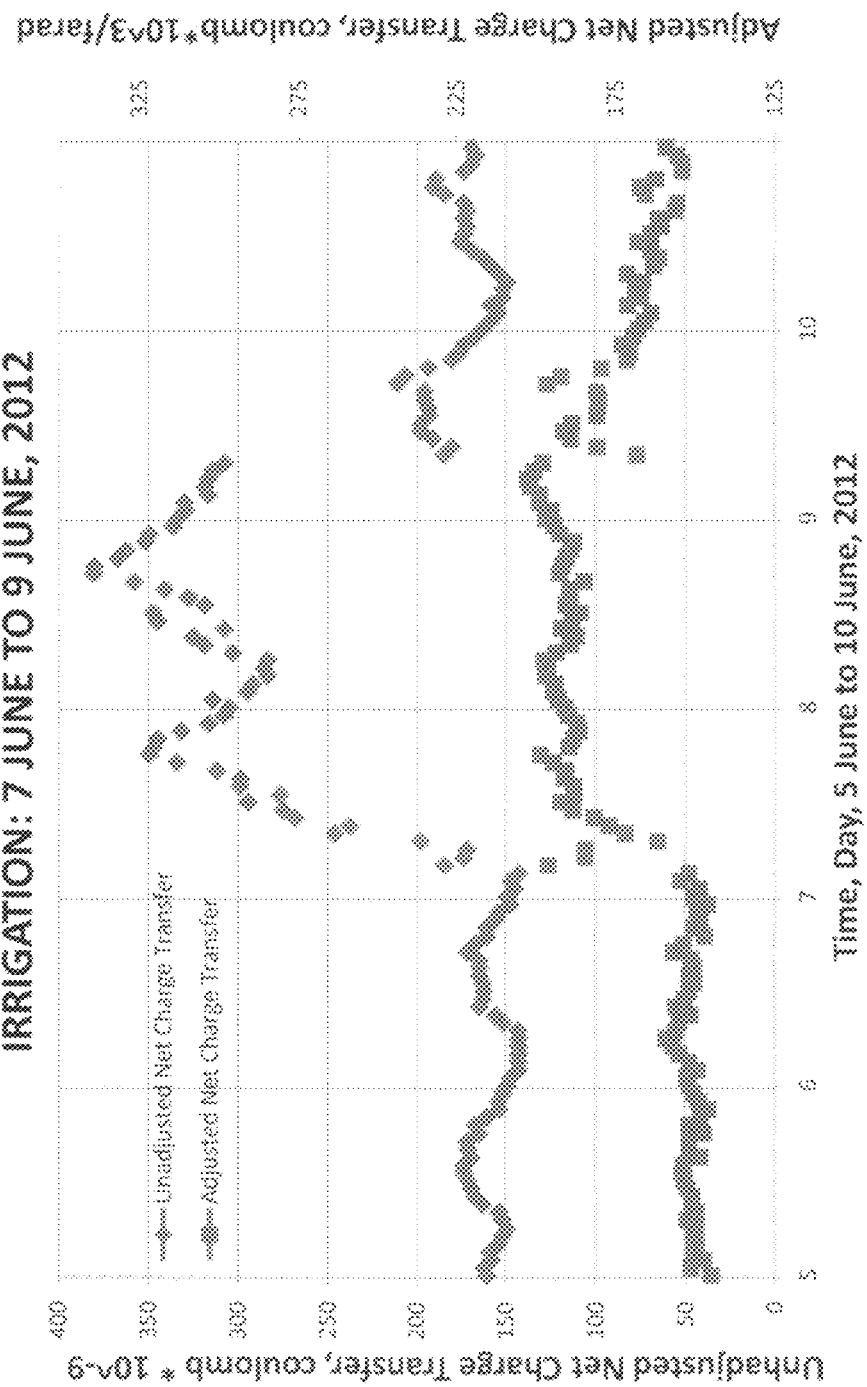
Figure 5B:
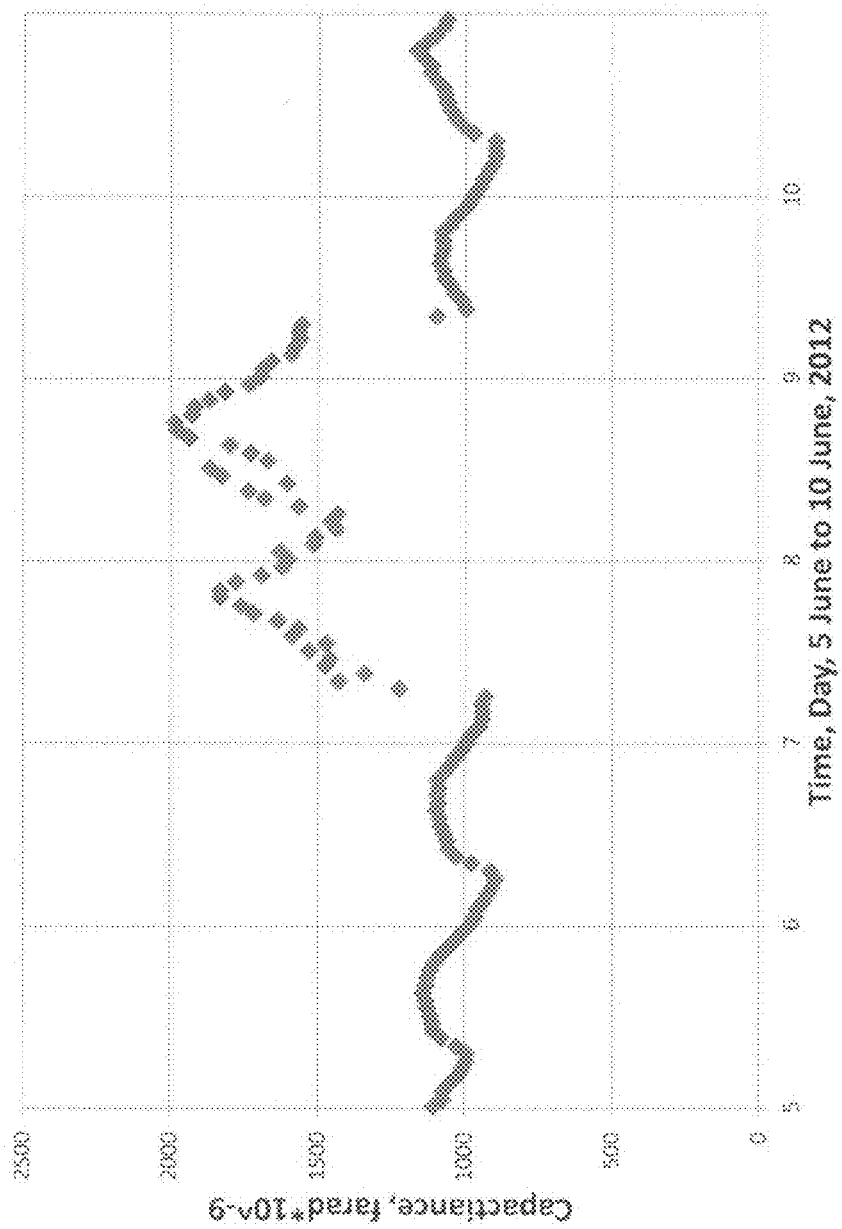
Figure 5C:
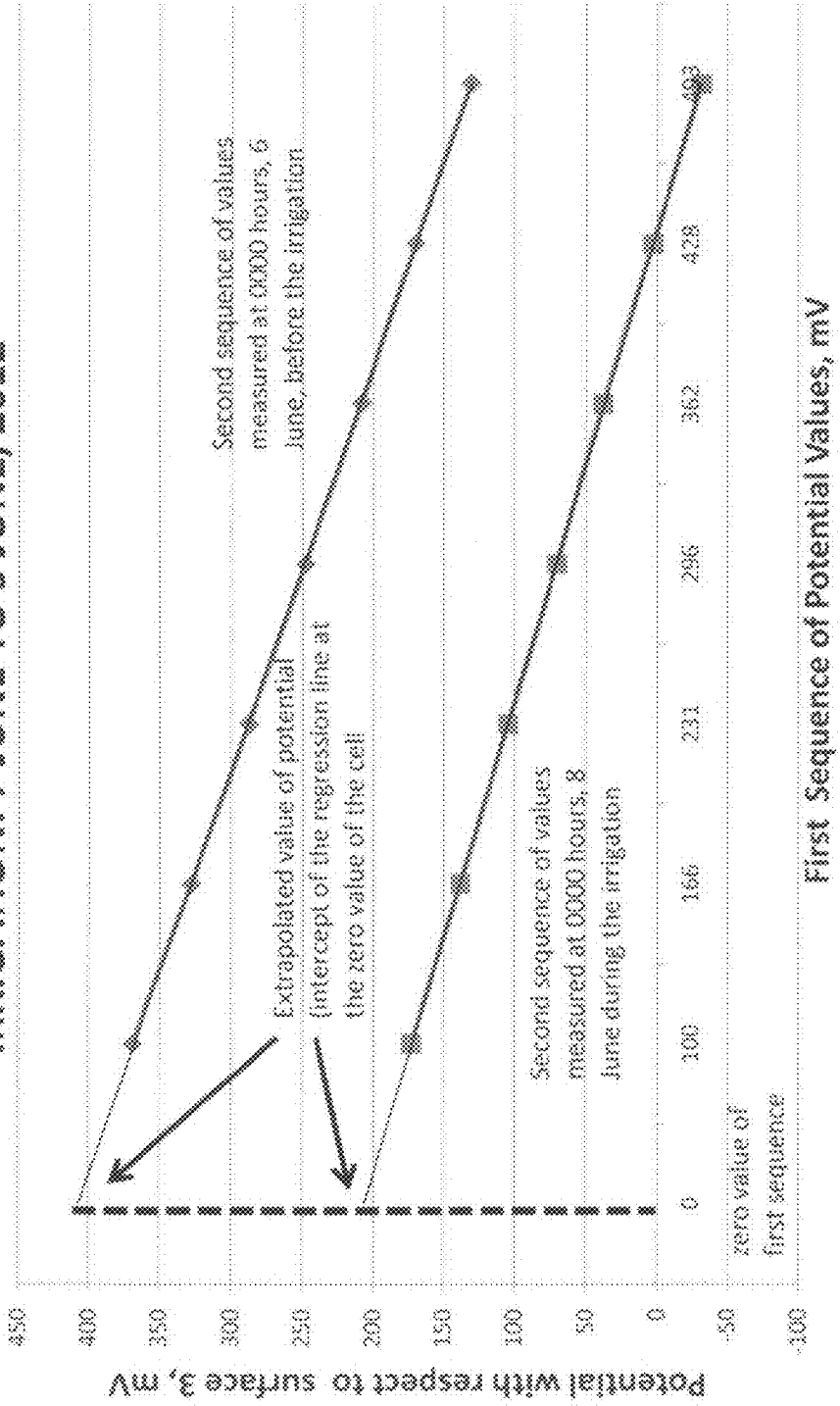
Figure 5D:
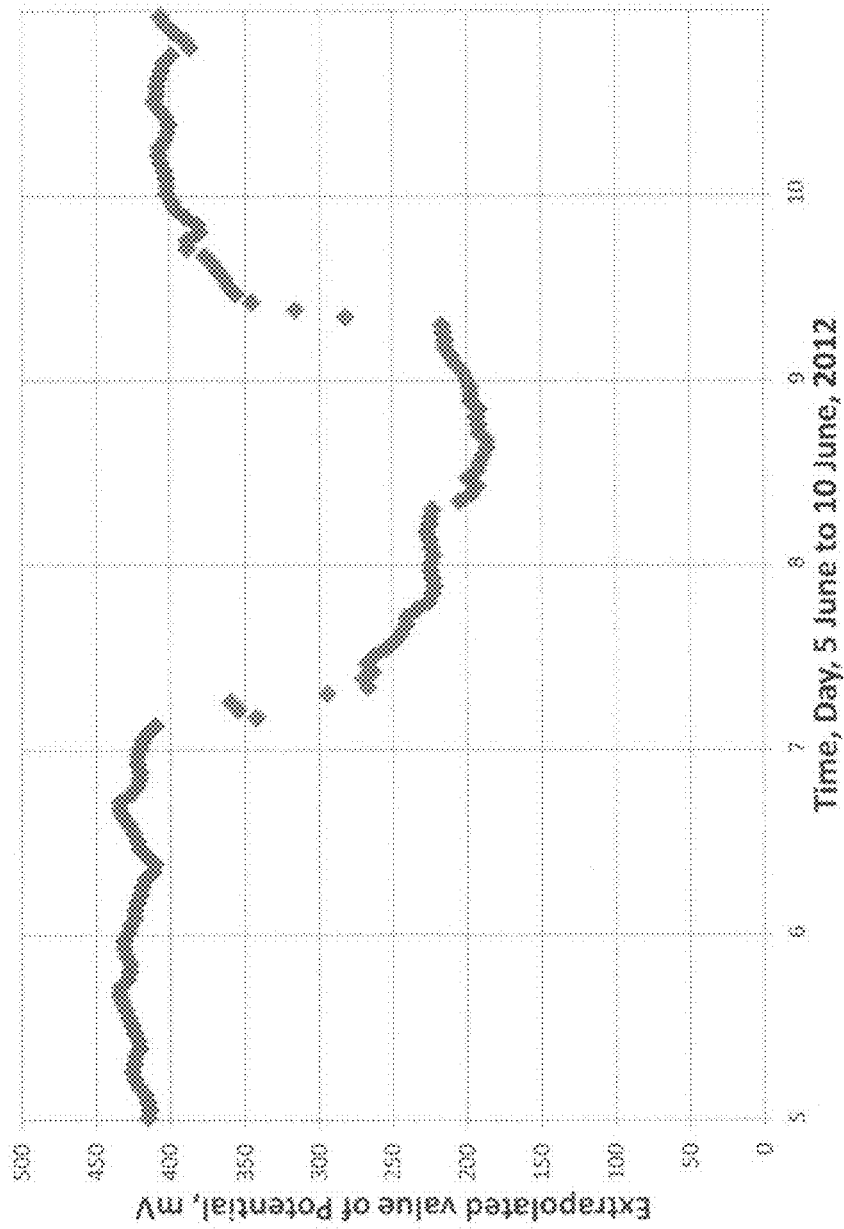

FIG. 5d gives the values of extrapolated potential every hour for the five day interval. This graph would be used by the Grower to determine amount and type fertilizer being taken up by the plant.

Example of the Measurements, Determination and Identification Illustrated in FIG. 5a-d in Terms of the Steps of the Claims Claim 1, Steps a and b: first surface 1 and second surface 2 are implanted in the trunk of the almond tree; third surface 3 implanted in the soil, FIG. 1

Claim 1, Step c: wires connected between surfaces and electronics, FIG. 1,

Claim 1, Step d: capacitance is measured between first surface 1 and third surface 3, result illustrated in FIG. 5b.

Claim 1, Step e: potential impressed between first surface 1 and second surface 2, Claim 1, Step f: net charge transfer measured, result illustrated in FIG. 5.a (diamonds)

Claim 1, Step g: adjusted net charge transfer formed from the ratio of measured unadjusted net charge transfer and measured capacitance, result illustrated in FIG. 5a (squares).

Claim 2, Step a: measuring a second sequence of potential values between first surface 1 and third surface 3, circuit path of measurement, FIG. 3c; result illustrated in FIG. 5c for a sequence before and during irrigation.

Claim 2, Step b: plotting value of second sequence of potential values, result illustrated in FIG. 5c before and during irrigation.

Claim 2, Step c: extrapolated value is the potential at the intercept of the regression line of the second sequence of potential values at zero net charge transfer for two specific hourly measurements, result illustrated in FIG. 5c. FIG. 5d gives the graph of extrapolated values for every hour during the five day interval.

The adjusted net charge transfer and the extrapolated values obtained at one hour intervals are illustrated in FIG. 5d. These two variables are the output variables stated in Claim 1, Step g and Claim 2, Step c, respectively.

Figure 6A:
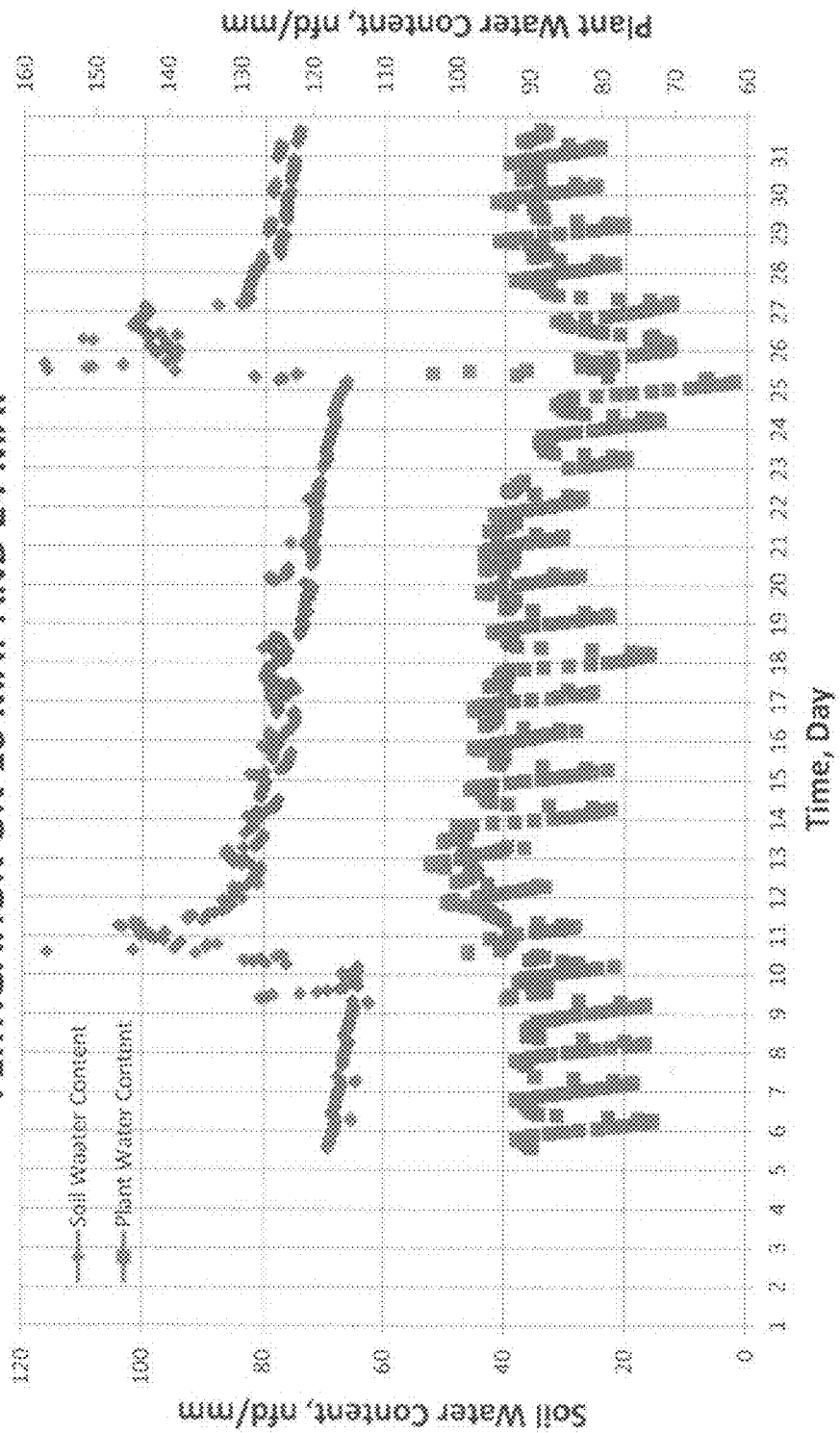

Example of Response of Adjusted Net Charge Transfer and Identification Potential to Fertigation, in Almonds, Madera County, California over a One Month Period Fertigation is the process of applying fertilizer impregnated water. In this example, both nitrogen and potassium were added to the irrigation water during two intervals in May in an almond Orchard in Madera County, California. The graphs in FIG. 6a and FIG. 6b illustrate the progression of the response from the soil through to the adjusted net charge transfer and extrapolated potential.

The orchard was fertigated on 10 May and 25 May with both nitrogen and potassium. FIG. 6a (diamonds) indicates the soil water content rose sharply with application and then declined in a roughly exponential form for the first water application. The response of the soil water content (squares in FIG. 6a) was an approximate square function over a two day period. The water content response to irrigation was superimposed on the normal diurnal water content cycles.

Figure 6B:
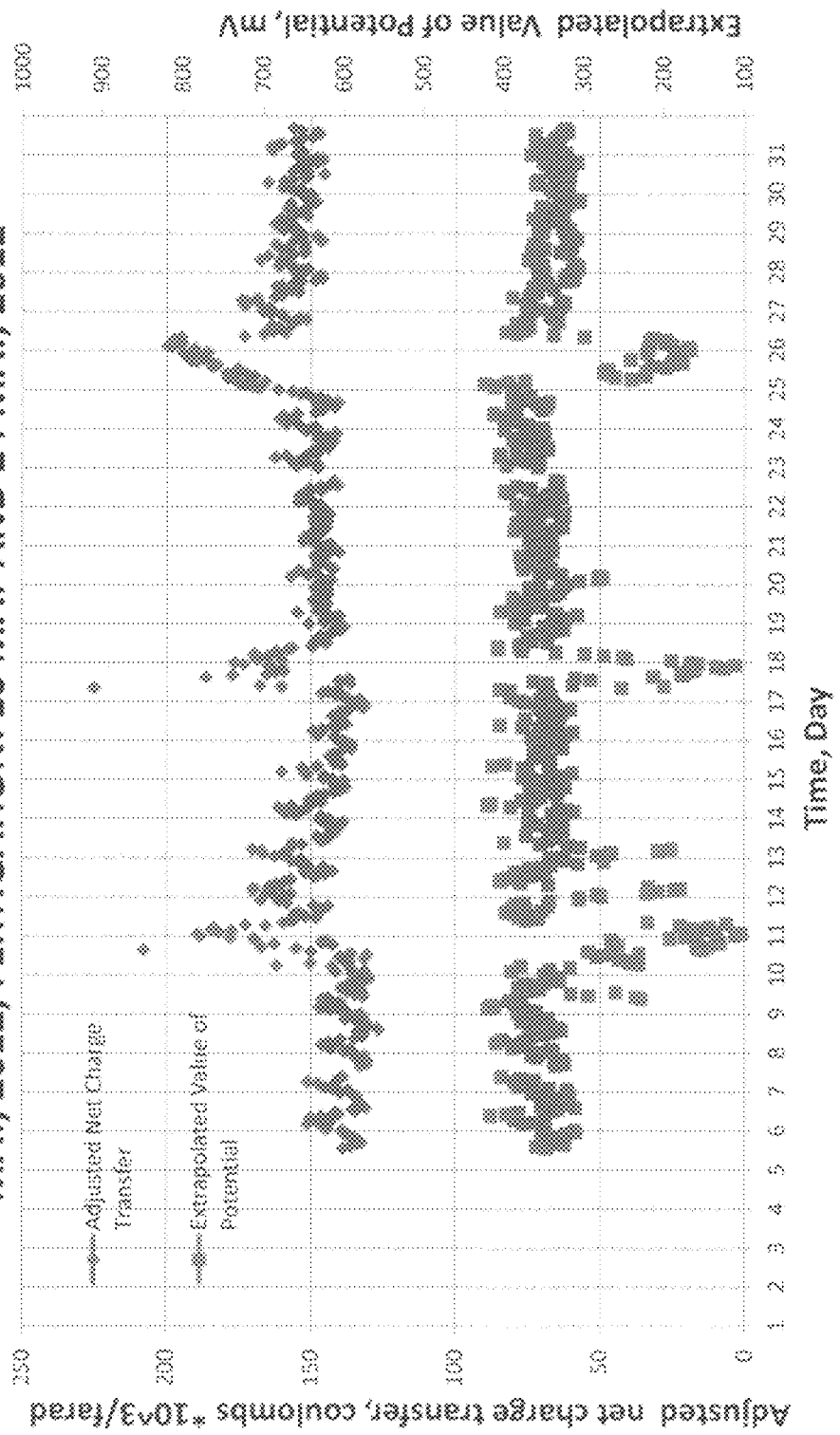

The adjusted net charge transfer and the identification potential obtained at one hour intervals are illustrated in FIG. 6b. These two variables are the output variables stated in Claim 1, Step g and claim 2, Step c, respectively.

Utility of the Apparatus and Methods of this Invention

Fertilizer is one of the two most important resource inputs in agriculture. This invention concerns the automatic, repetitive measurement of nutrient uptake into the plant. The measurements are timely. This permits their use by agricultural management for daily decisions concerning nutrient application. Furthermore, the measurements can be made over the full calendar year in perennial crops and in annual crops for periods of significant resource input. As such it permits manipulations of this resource to achieve maximum yield at the lowest cost and at the smallest environmental impact.

A specific example of the use of this apparatus and methods is to determine the duration of application of a fertilizer such as nitrate. Nitrate is applied on a daily basis and the uptake is measured on a daily basis. When the plant stops taking up the nitrate, application stops.

CONCLUSIONS, RAMIFICATIONS AND SCOPE OF INVENTION

The Apparatus and Methods which have been described can make separate, automatic, simultaneous, non destructive measurements of electrical capacitance and ion population as well as the identification of the type of ion causing the rise in ion population.

The essential characteristic of the apparatus and methods is the'implant of "windows" inside-the-plant. First surface 1 and second surface 2 function as windows facing a mass of normal cells. As such they can be used to observe the activities of these cells. The size of the "window" is quantified by the measurement of wetted area of the surfaces. This is a fundamental difference from prior art.

While the above description has many specificities, these should not be construed as limitations on the scope of the invention but rather as an exemplification of one preferred embodiment thereof.

For example, the surfaces can be round and rod-like and implanted in the tissue individually. Alternately, they can be arrayed as surfaces on an electronic chip wherein the chip is implanted in the tissue and the connections to external electronics made through planar traces passing out of the chip. A more advanced method would be to place microelectronics within the plant and implement the methods from within the plant.

The surfaces can be planar and reduced in size to the sub micron level such that specific tissue can be monitored.

The specification has been written in terms of a medium in the root zone of normal soil. The apparatus and methods can function as described in a hydroponic root zone as well.

The specification has been written in terms of a single dominant ion in the volume between the two surfaces within the plant. It is possible to interpret the results in the same manner as described considering the relative influence of two or more ions according to their relative populations (Bockris and Reddy, Volume 2, Eqn. 10.88).

REFERENCE NUMERALS IN FIGURES

1 First surface 1
2 Second surface 2
3 Third surface 3
4 Plant
5 Soil
6 Total surface area of first surface 1
7 Wetted area of first surface 1
8 Dry area of first surface 1
9 Charge transfer area on first surface 1
10 Charge transfer area on second surface 2
11 Wire connecting electronics to first surface 1
12 Wire connecting electronics to second surface 2
13 Wire connecting electronics to third surface 3
14 Electronics
15 Charge transfer path between first surface 1 and second surface 2
16 Charge transfer path between first surface 1 and third surface 3

FIGURE CAPTIONS

FIG. 1. An example of first surface 1 and second surface 2 implanted in the sapwood of a Pistachio Tree, Cochise County, Arizona. First surface 1 and second surface 2 extend radially into the trunk through the white nylon drill guide. Outside the trunk the two surfaces bend downward and mate with wire 11 and wire 12, respectively. The active surface within the trunk is 10 mm in length.

FIG. 2. Schematic Diagram of Surfaces Implanted Within Plant 4 and Soil 5
Electrochemical Circuit Paths FIG. 3a. Electrochemical Circuit Path for the impressed potential between first surface 1 and second surface 2. The energy flow in this path is from electronics 14 to plant 4

FIG. 3b. Electrochemical Circuit Path for the measurement of capacitance between wire 11 and wire 13. The energy flow in this path is from plant 4 to electronics 14. This path is operational only when there is a zero net charge transfer in the path illustrated in FIG. 3a. This fact is emphasized in the omission of second surface 2 in this figure.

FIG. 3c. Electrochemical Circuit Path for the measurement of potential between wire 11 (first surface 1) and wire 13 (third surface 3). The energy flow in this path is from plant 4 to electronics 14. This path is operational only when there is a finite, non zero net charge transfer in the path illustrated in FIG. 3a. The fact is emphasized by inclusion in the figure of a path 15 from first surface 1 to second surface 2
Surface Area Considerations FIG. 4a. Illustration of the wetted area 7 and dry area 8 within the total surface area 6 of first surface 1. The wetted surface area 7 is used in this invention because it is proportional to the wetted area. The total surface area 6 is employed in the apparatus and method of U.S. Pat. No. 6,870,376.

FIG. 4b. Illustration of charge transfer through wetted area 7 of first surface 1 and wetted area 10 of second surface 2. There is no charge transfer across dry area 8 of first surface 1.
Example of Adjusted Net Charge Transfer Before, During and after Irrigation and Identifying Extrapolated Value Before and During Irrigation; Five Day Time Scale FIG. 5a. Example of unadjusted and adjusted net charge transfer before, during and after an irrigation in an Almond Orchard In California. Uptake of ions came from residual nitrogen in the root zone.

FIG. 5b. Example of electrical capacitance measurement before, during and after an irrigation in an Almond Orchard In California FIG. 5c. Example of the second sequence of potential values before and during the irrigation. The regression line is extrapolated to the value which would exist at zero net charge transfer. This is the intercept potential indicated by the dashed line in the figure.

FIG. 5d. Example of hourly values of adjusted net charge transfer and extrapolated potential
Example of Response of Net Charge Transfer and Extrapolated Value to Fertigation; Thirty Day Time Scale FIG. 6a. Soil and plant water content over two fertigation cycles.

FIG. 6b. Adjusted net charge transfer and extrapolated values.

I claim:

1. A method for measuring ion population within a plant comprising the steps of:
   (a) placing a first surface and a second surface within said plant,
   (b) placing a third surface in the root environment of said plant,
   (c) connecting a first wire to said first surface, connecting a second wire to said second surface, connecting a third wire to said third surface,
   (d) measuring electrical capacitance between said first wire and said third wire wherein said electrical capacitance is proportional to the wetted surface area of said first surface,
   (e) impressing a first sequence of potential values between said first wire and said second wire,
   (f) measuring a sequence of charge values passing through said first wire for each step of said first sequence,
   (g) forming the ratio of a value in said sequence of charge values to said electrical capacitance whereby said ratio is a measure of said ion population in said plant which is adjusted for the surface area across which net charge transfer occurs.

2. In claim 1 further including
   (a) measuring a second sequence of potential values between said first wire and said third wire connected to said third surface, (b) plotting said second sequence of potential values against said first sequence of potential values,
(c) extrapolating to the value of said second sequence of potential at zero value of said first sequence of potential whereby said extrapolated value identifies said type of ion.

3. Apparatus for measuring ion population and identifying the type of ion within a plant comprising:
(a) means for implanting first surface within said plant, second surface within said plant, third surface in root environment,
(b) first wire connected to said first surface, second wire connected to said second surface, third wire connected to said third surface,
(c) means coupled to said first wire and said third wire for measuring value of electrical capacitance generated therebetween by said plant,
(d) means coupled to said first wire and said second wire for generating a first electrical potential therebetween,
(e) means for measuring charge passing through said first wire,
(f) means for measuring a second electrical potential between said first wire and said third wire,
(g) means for plotting said second electrical potential against said first electrical potential.

4. Apparatus as recited in claim 3 further including a plurality of means for implanting said first surface within said plant, means for implanting second surface within said plant, means for implanting third surface in root environment and means interposed between each of said first surface, said second surface and said third surface for selectively connecting each one of said first surface, said second surface and said third surface to said measuring means.

* * * * *